United States Patent
Tendo et al.

(10) Patent No.: US 7,795,458 B2
(45) Date of Patent: Sep. 14, 2010

(54) SALT OF (2S, 3S)-3-[[(1S)-1-ISOBUTOXYMETHYL-3-METHYLBUTYL]CARBAMOYL]OXIRANE-2-CARBOXYLIC ACID

(75) Inventors: Atsushi Tendo, Kasukabe (JP); Toshihiro Takahashi, Misato (JP); Tomio Yamakawa, Kashiwa (JP); Kazuki Okai, Koshigaya (JP); Susumu Nihashi, Sakura (JP)

(73) Assignee: Nippon Chemiphar Co., Ltd, Chiyoda-ku, Tokyo (JP)

( * ) Notice: Subject to any disclaimer, the term of this patent is extended or adjusted under 35 U.S.C. 154(b) by 0 days.

(21) Appl. No.: 12/545,665

(22) Filed: Aug. 21, 2009

(65) Prior Publication Data

US 2009/0312563 A1    Dec. 17, 2009

Related U.S. Application Data

(63) Continuation of application No. 10/553,946, filed as application No. PCT/JP2004/005767 on Apr. 22, 2004, now Pat. No. 7,585,988.

(30) Foreign Application Priority Data

Apr. 25, 2003   (JP)   ............................. 2003-121103

(51) Int. Cl.
   *C07D 303/48*   (2006.01)
(52) U.S. Cl. ........................ 549/549; 549/541
(58) Field of Classification Search ................ 549/541, 549/549

See application file for complete search history.

(56) References Cited

U.S. PATENT DOCUMENTS

| | | |
|---|---|---|
| 5,614,632 A | 3/1997 | Bhupathy et al. |
| 5,705,496 A | 1/1998 | Polansky |
| 6,313,289 B1 | 11/2001 | Ludescher et al. |
| 6,387,908 B1 | 5/2002 | Nomura et al. |
| 6,682,913 B1 | 1/2004 | Jekkel et al. |
| 6,696,599 B2 | 2/2004 | Jekkel et al. |
| 6,713,491 B2 | 3/2004 | Orlandi |
| 2002/0091131 A1* | 7/2002 | Nomura et al. ........ 514/255.05 |
| 2003/0008899 A1 | 1/2003 | Orlandi |
| 2003/0207413 A1 | 11/2003 | Jekkel et al. |
| 2004/0039225 A1 | 2/2004 | Jekkel et al. |

FOREIGN PATENT DOCUMENTS

JP    62-108877 A    5/1987

OTHER PUBLICATIONS

International Search Report, PCT/JP2004/005767, Aug. 3, 2004.
Stahl et al., "Handbook of Pharmaceutical Salts, Properties, Selection, and Use", International Union of Pure and Applied Chemistry (IUPAC), 2002.

* cited by examiner

*Primary Examiner*—Janet L Andres
*Assistant Examiner*—David E Gallis
(74) *Attorney, Agent, or Firm*—Nixon Peabody LLP; Jeffrey L. Costellia

(57) ABSTRACT

The invention relates to purification of (2S,3S)-3-[[(1S)-1-isobutoxymethyl-3-methylbutyl]carbamoyl]oxirane-2-carboxylic acid [hereinafter, referred to as the carboxylic acid] using the salt of the carboxylic acid with an organic amine selected from the group consisting of piperazine, adamantane amines and others. The invention also relates to providing crystalline sodium salt of the carboxylic acid. The sodium salt is usable as a material for preparing medicaments and improved in storage stability, and has the following characteristics:

DSC: exothermic peak observed at a temperature in the range of 170 to 175° C. with weight decrease; and characteristic absorption bands of infrared absorption spectrum (KBr tablet) 3255, 2950, 2860, 1670, 1630, 1550, 1460, 1435, 1395, 1365, 1310, 1260, 1110, 890 $cm^{-1}$.

1 Claim, No Drawings

SALT OF (2S, 3S)-3-[[(1S)-1-ISOBUTOXYMETHYL-3-METHYLBUTYL] CARBAMOYL] OXIRANE-2-CARBOXYLIC ACID

FIELD OF THE INVENTION

The present invention relates to a salt of (2S,3S)-3-[[(1S)-1-isobutoxymethyl-3-methylbutyl]carbamoyl]-oxirane-2-carboxylic acid.

BACKGROUND OF THE INVENTION

The below-illustrated sodium (2S,3S)-3-[[(1S)-1-isobutoxymethyl-3-methylbutyl]carbamoyl]-oxirane-2-carboxylate (hereinafter referred to as Compound A) shows a cathepsin-inhibitory action and is useful as a remedy for treating rheumatoid arthritis and osteoporosis (Patent reference 1: WO 99/11640 pamphlet):

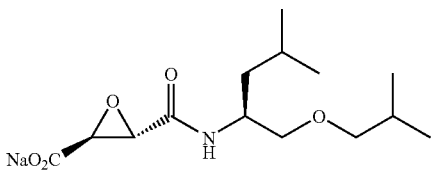

Patent reference 1 describes a process for producing Compound A according to the following reaction scheme (see Example 48 of Patent reference 1):

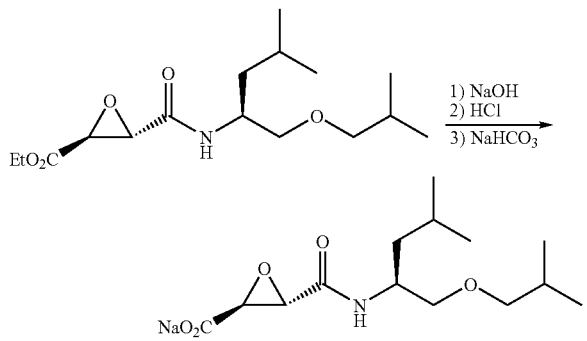

The starting ester material of the above-mentioned reaction scheme is generally purified by column chromatography to obtain a purified Compound A.

DISCLOSURE OF THE INVENTION

Amorphous Compound A is so hygroscopic and so thermally unstable that various troubles in producing the remedy are expected, and is hence difficult to treat as material for the pharmaceutical preparation. Accordingly, there is a need to provide a thermally stable crystalline (2S,3S)-3-[[(1S)-1-isobutoxymethyl-3-methylbutyl]carbamoyl]oxirane-2-carboxylic acid salt having a long storage-life.

If crystalline Compound A is prepared according to the conventional recrystallization or salt-making process in which Compound A is converted from a free form into the desired form, the product often precipitates in the form of too fine crystallites to filter or occasionally in the form of agar-like jelly. Further, since Compound A is very hygroscopic, moisture in air causes to conversion of Compound A from the crystal state into the amorphous state and, as a result, the filterability of the product lowers.

In the industrial preparation of Compound A, purification by column chromatography is a troublesome procedure. Accordingly, it is also desired to provide a simple purification process for Compound A.

When Compound A is prepared in an industrial scale, it is important to purify Compound A in the free acid form. As described hereinafter, it is very simple and industrially advantageous to prepare Compound A in the free acid form from the after-described organic amine salt. In addition, it makes the preparation process further simple and advantageous that Compound A in an ester form is hydrolyzed with a basic sodium or potassium compound to convert directly into a sodium or potassium salt.

The present invention has an object to provide a thermally stable crystalline sodium or potassium (2S,3S)-3-[[(1S)-1-isobutoxymethyl-3-methylbutyl]carbamoyl]-oxirane-2-carboxylate having a long storage-life. The invention also has objects to provide a simple and industrially advantageous process for preparing crystallites of the above-mentioned compound and to provide a salt of the compound with an organic amine employable in the process.

The invention relates to crystalline sodium (2S,3S)-3-[[(1S)-1-isobutoxymethyl-3-methylbutyl]carbamoyl]-oxirane-2-carboxylate having the following characteristics:

DSC: an exothermic peak observed at a temperature in the range of 170 to 175° C. with weight decrease; and characteristic absorption bands of infrared absorption spectrum (KBr tablet): 3255, 2950, 2860, 1670, 1630, 1550, 1460, 1435, 1395, 1365, 1310, 1260, 1110, 890 cm$^{-1}$.

The invention also relates to crystalline potassium (2S,3S)-3-[[(1S)-1-isobutoxymethyl-3-methylbutyl]carbamoyl]oxirane-2-carboxylate having the following characteristics:

DSC: an exothermic peak observed at 177° C. with weight decrease; and characteristic absorption bands of infrared absorption spectrum (KBr tablet): 3270, 3080, 2950, 2870, 1680, 1625, 1560, 1460, 1380, 1300, 1240, 1110, 895 cm$^{-1}$.

The invention further relates to a process for preparation of crystalline sodium or potassium (2S,3S)-3-[[(1S)-1-isobutoxymethyl-3-methylbutyl]carbamoyl]oxirane-2-carboxylate, comprising the following steps (1) to (6):

(1) hydrolyzing (2S,3S)-3-[[(1S)-1-isobutoxymethyl-3-methylbutyl]carbamoyl]oxirane-2-carboxylic acid in an ester form, to obtain (2S,3S)-3-[[(1S)-1-isobutoxymethyl-3-methylbutyl]carbamoyl]oxirane-2-carboxylic acid, (2) causing the carboxylic acid obtained in the preceding step react with an organic amine, to prepare a salt of (2S,3S)-3-[[(1S)-1-isobutoxymethyl-3-methylbutyl]carbamoyl]oxirane-2-carboxylic acid with the organic amine, (3) adding an acid to the salt obtained in the preceding step, to obtain (2S,3S)-3-[[(1S)-1-isobutoxymethyl-3-methylbutyl]carbamoyl]oxirane-2-carboxylic acid, (4) causing the carboxylic acid obtained in the preceding step react with a basic sodium or potassium compound in a mixed solvent of water and an aliphatic alcohol or acetone, to obtain a sodium or potassium salt, (5) recrystallizing the sodium or potassium salt obtained in the preceding step using an aliphatic alcohol, and (6) drying the product recrystallized in the preceding step under reduced pressure.

The invention furthermore relates to a process for preparation of crystalline sodium or potassium (2S,3S)-1-isobutoxymethyl-3-methylbutyl]carbamoyl]oxirane-2-carboxylate, comprising the following steps (1) to (4):

(1) causing (2S,3S)-3-[[(1S)-1-isobutoxymethyl-3-methylbutyl]carbamoyl]oxirane-2-carboxylic acid in an ester form react with a basic sodium or potassium compound, to obtain sodium or potassium (2S,3S)-3-[[(1S)-1-isobutoxymethyl-3-methylbutyl]carbamoyl]oxirane-2-carboxylate, (2) crystallizing the sodium or potassium salt obtained in the preceding step from a mixed solvent of water and acetone, to obtain crystalline sodium or potassium salt, (3) recrystallizing the sodium or potassium salt obtained in the preceding step using an aliphatic alcohol, and (4) drying the product recrystallized in the preceding step under reduced pressure.

The invention still further relates to a salt of (2S,3S)-3-[[(1S)-1-isobutoxymethyl-3-methylbutyl]carbamoyl]oxirane-2-carboxylic acid with an organic amine.

The invention further relates to a salt of (2S,3S)-3-[[(1S)-1-isobutoxymethyl-3-methylbutyl]carbamoyl]-oxirane-2-carboxylic acid with an organic amine represented by the formula of:

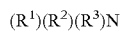

$(R^1)(R^2)(R^3)N$ in which $R^1$ is hydrogen or a linear-chain, branched-chain or cyclic alkyl group having 1 to 10 carbon atoms; $R^2$ is hydrogen or a linear-chain, branched-chain or cyclic alkyl or aralkyl group of 1 to 10 carbon atoms; and $R^3$ is a linear-chain, branched-chain or cyclic alkyl group of 1 to 10 carbon atoms which may have a substituent group selected from the group consisting of halogen atoms, nitro, hydroxyl, carboxyl, guanidino, amino and aralkyl-amino groups; or otherwise $R^2$ and $R^3$ can be combined to form a 5- to 7-membered ring comprising the nitrogen atom to which $R^2$ and $R^3$ are connected (the ring may contain additional nitrogen atom).

The invention further relates to a salt of (2S,3S)-3-[[(1S)-1-isobutoxymethyl-3-methylbutyl]carbamoyl]-oxirane-2-carboxylic acid with an organic amine selected from the group consisting of piperazine, adamantane amines, cyclohexylamine, dicyclohexylamine, tris(hydroxy-methyl)aminomethane, arginine, lysine, benzathine and meglumine.

MOST PREFERRED EMBODIMENTS OF THE INVENTION

The present invention is explained below in more detail.

Crystalline sodium or potassium (2S,3S)-3-[[(1S)-1-isobutoxymethyl-3-methylbutyl]carbamoyl]oxirane-2-carboxylate of the invention can be obtained according to the following flow chart.

(Flow Chart)

Process 1:

ester form (A)→free form (B)→salt with an organic amine (C)→free form (D)→Na or K salt (E)→recrystallized product (F)→immediately dried crystallites (G);

or otherwise

Process 2:

ester form (A)→Na or K salt (E)→recrystallized product (F)→immediately dried crystallites (G).

Each step is explained below.

(Process 1)

(1) Step of Ester Form (A)→Free Form (B)

In a mixed solvent of water and an aliphatic alcohol such as methanol, ethanol or isopropyl alcohol, (2S,3S)-3-[[(1S)-1-isobutoxymethyl-3-methylbutyl]carbamoyl]-oxirane-2-carboxylic ester (A) is hydrolyzed in the presence of a base such as sodium hydroxide or potassium hydroxide, and is then neutralized to obtain (2S,3S)-3-[[(1S)-1-isobutoxymethyl-3-methylbutyl]carbamoyl]oxirane-2-carboxylic acid [free form (B)].

In the above procedure, the starting (2S,3S)-3-[[(1S)-1-isobutoxymethyl-3-methylbutyl]carbamoyl]oxirane-2-carboxylic ester is an ester with an aliphatic alcohol, preferably an ester with a primary, secondary or tertiary alcohol having 1 to 6 carbon atoms, more preferably an ester with ethanol, methanol, n-propyl alcohol or isopropyl alcohol.

For synthesizing the ester of the starting material, (2S,3S)-3-alkoxycabonyloxirane-2-carboxylic acid and (1S)-1-isobutoxymethyl-3-methylbutylamine are, for example, condensed according to the normal condensation process (e.g., DCC-HOSu method, acid chloride method, and acid anhydride method).

(2) Step of Free Form (B)→Salt with an Organic Amine (C)

The free form (B) prepared in Step (1) is caused to react with an organic amine in a solvent. Examples of the solvents include aliphatic alcohols such as methanol, ethanol, n-propyl alcohol and isopropyl alcohol; aliphatic ethers such as diethyl ether and diisopropyl ether; aliphatic esters such as ethyl acetate; aliphatic ketones such as acetone and ethyl methyl ketone; and water. They may be used singly or may be mixed. In consideration of flammability and toxicity, the solvent preferably is ethyl acetate, acetone, water or a mixture thereof. Thus, the salt with a desired organic amine can be obtained.

The organic amine is, for example, represented by the formula of:

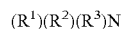

$(R^1)(R^2)(R^3)N$ in which $R^1$ is hydrogen or a linear-chain, branched-chain or cyclic alkyl group having 1 to 10 carbon atoms; $R^2$ is hydrogen or a linear-chain, branched-chain or cyclic alkyl or aralkyl group of 1 to 10 carbon atoms; and $R^3$ is a linear-chain, branched-chain or cyclic alkyl group (including a crosslinked cyclic hydrocarbon group such as adamantyl) having 1 to 10 carbon atoms which may have a substituent selected from the group consisting of halogen atoms, nitro, hydroxyl, carboxyl, guanidino, amino and aralkylamino groups; or otherwise $R^2$ and $R^3$ can be combined to form a 5- to 7-membered ring comprising the nitrogen atom to which $R^2$ and $R^3$ are connected (the ring may contain additional nitrogen atom). In consideration of cost, toxicity and crystallization, the organic amine preferably is piperazine, an adamantane amine, cyclohexylamine, dicyclohexylamine, tris(hydroxymethyl)aminomethane, arginine (preferably in L-form), lysine (preferably in D-form or DL-form), benzathine or meglumine. The salts with D- or DL-lysine, benzathine, meglumine and tris (hydroxymethyl)aminomethane can be immediately used as medicaments without further processing.

(3) Step of Salt with an Organic Amine (C)→Free Form (D)

The salt with an organic amine (C) obtained in Step (2) is treated with an acid (e.g., hydrochloric acid) in the conventional manner, to obtain (2S,3S)-3-[[(1S)-1-isobutoxymethyl-3-methylbutyl]carbamoyl]oxirane-2-carboxylic acid (D) of high purity. Thus obtained free form (D) gave no peak attributed to cleavage products (9.8 minutes, see Example 14) while the peak is given by the free form or the metal salt thereof obtained by hydrolyzing the ester form (A) purified by silica-gel column chromatography.

(In the Case of Preparing a Sodium Salt)

(4) Step of Free Form (D)→Na Salt (E)

The free form (D) is converted into a sodium salt using a sodium source in an organic solvent capable of dissolving the free form (D) or in a water-containing organic solvent. Examples of the sodium sources include sodium metal, sodium alkoxides such as sodium methoxide and sodium ethoxide, sodium hydroxide, sodium carbonate, and sodium organic carboxylate.

The solvent preferably is a mixed solvent of water and methanol, ethanol or acetone, in consideration of flammability and toxicity. If the water content is in the range of 1 to 5%, the product is obtained in a high yield.

Thus obtained solid product is well filtered so that the product is collected by conventional filtration.

(5) Step of Na Salt (E)→Recrystallized Product (F)

The solid sodium salt (E) obtained in Step (4) is dissolved in an aliphatic alcohol such as methanol at a temperature of form room temperature to 60° C., and then an organic solvent is added to precipitate a crystalline product. The organic solvent preferably is a mixed solvent of ethyl acetate, methanol and ethanol, in consideration of flammability and toxicity. If the mixing ratio of ethyl acetate/alcohol is in the range of 10/1 to 5/1, the product is obtained in a high yield.

Thus recrystallized product (F) is well filtered so that the product is collected by conventional filtration.

(6) Recrystallized Product (F)→Immediately Dried Crystallites (G)

The recrystallized product (F) is collected by filtration in a stream of nitrogen gas, and immediately dried to obtain, in a high yield, crystalline sodium (2S,3S)-3-[[(1S)-1-isobutoxymethyl-3-methylbutyl]carbamoyl]oxirane-2-carboxylate (G) of high purity having the following characteristics:

DSC (the same as that in Example 15): exothermic peak observed in the range of 170 to 175° C. with weight decrease; and characteristic absorption bands of infrared absorption spectrum (KBr tablet): 3255, 2950, 2860, 1670, 1630, 1550, 1460, 1435, 1395, 1365, 1310, 1260, 1110, 890 cm$^{-1}$.

The product preferably is in the form of white crystalline needles.

The crystalline Na salt of the invention (described in Example 9) was subjected to a comparative stability test. In the test, the Na salt was left at 80° C. for three days together with both the substance obtained by condensing the solution to dryness and the product collected by filtration and left at room temperature after recrystallization. As a result, it was found that the Na salt of the invention was superior to the substances for comparison in storage stability (see Example 15).

(In the Case of Preparing a Potassium Salt)

(7) Step of Free Form (D)→K Salt (E)

The free form (D) is converted into a potassium salt using a potassium source in an organic solvent capable of dissolving the free form (D) or in a water-containing organic solvent. Examples of the potassium sources include potassium metal, potassium alkoxides such as potassium methoxide and potassium ethoxide, potassium hydroxide, potassium carbonate, and potassium organic carboxylate.

The solvent preferably is a mixed solvent of water and methanol, ethanol or acetone, in consideration of flammability and toxicity. If the water content is in the range of 1 to 5%, the product is obtained in a high yield.

Thus obtained solid product is well filtered so that the product is collected by conventional filtration.

(8) Step of K Salt (E)→Recrystallized Product (F)

The solid potassium salt (E) obtained in Step (7) is dissolved in an aliphatic alcohol such as methanol at a temperature from room temperature to 60° C., and then an organic solvent is added to precipitate a crystalline product. The organic solvent preferably is a mixed solvent of ethyl acetate, methanol and ethanol, in consideration of flammability and toxicity. If the mixing ratio of ethyl acetate/alcohol is in the range of 30/1 to 10/1, the product is obtained in a high yield.

Thus recrystallized product (F) is well filtered so that the product is collected by conventional filtration.

(9) Recrystallized Product (F)→Immediately Dried Crystallites (G)

The recrystallized product (F) is collected by filtration in a stream of nitrogen gas, and immediately dried to obtain, in a high yield, crystalline potassium (2S,3S)-3-[[(1S)-1-isobutoxymethyl-3-methylbutyl]carbamoyl]oxirane-2-carboxylate (G) of high purity having the following characteristics:

DSC (the same as that in Example 15): exothermic peak observed at 177° C. with weight decrease; and characteristic absorption bands of infrared absorption spectrum (KBr tablet): 3270, 3080, 2950, 2870, 1680, 1625, 1560, 1460, 1380, 1300, 1240, 1110, 895 cm$^{1}$.

The product is preferably in the form of white crystalline needles.

The crystalline K salt of the invention (described in Example 11) was subjected to a stability test in which the K salt was left at 80° C. for three days. As a result, it was found that the K salt of the invention was excellent in storage stability (see Example 15).

(In the Case of Preparing a Calcium or Lithium Salt)

Crystalline calcium or lithium (2S,3S)-3-[[(1S)-1-isobutoxymethyl-3-methylbutyl]carbamoyl]oxirane-2-carboxylate of high purity can be prepared in a high yield through the steps similar to the above-mentioned Steps (4) to (9).

(Process 2)

(1) Ester Form (A)→Na or K Salt (E)

[Preparation of Na Salt (E)]

The Na salt (E) can be obtained by causing the ester form (A) described in Step (1) of Process 1 react with a basic sodium compound (e.g., sodium carbonate, sodium hydroxide) to hydrolyze, by condensing the reaction mixture, and then by adding a water-compatible organic solvent such as acetone to crystallize the salt. If the water content is in the range of 1 to 5%, the product is obtained in a high yield.

[Preparation of K Salt (E)]

The K salt (E) can be obtained by causing the ester form (A) react with a basic potassium compound (e.g., potassium carbonate, potassium hydroxide) to hydrolyze, by condensing the reaction mixture, and then by adding a water-compatible organic solvent such as acetone to crystallize the salt. If the water content is in the range of 1 to 5%, the product is obtained in a high yield.

(2) Na or K Salt (E)→Recrystallized Product (F)→Immediately Dried Crystallites (G)

The steps of Na salt (E)→recrystallized product (F)→immediately dried crystallites (G) can be the same as Steps (5) and (6) of Process 1 described above.

The steps of K salt (E)→recrystallized product (F)→immediately dried crystallites (G) can be the same as Steps (8) and (9) of Process 1 described above.

As described above, the purification process in which (2S, 3S)-3-[[(1S)-1-isobutoxymethyl-3-methylbutyl]-carbamoyl] oxirane-2-carboxylic acid is converted to a salt with an organic amine, as well as the process in which the ester form of (2S,3S)-3-[[(1S)-1-isobutoxymethyl-3-methylbutyl]carbamoyl]oxirane-2-carboxylic acid is hydrolyzed with a basic sodium or potassium compound to prepare directly a sodium or potassium (2S,3S)-3-[[(1S)-1-isobutoxymethyl-3-methylbutyl]carbamoyl]oxirane-2-carboxylate, does not need to involve the step for purifying the ester form by silica-gel column chromatography. They are, therefore, simple and industrially advantageous processes for purifying (2S,3S)-3-[[(1S)-1-isobutoxymethyl-3-methylbutyl]carbamoyl]oxirane-2-carboxylic acid.

The crystalline sodium or potassium (2S,3S)-3-[[(S)-1-isobutoxymethyl-3-methylbutyl]carbamoyl]oxirane-2-carboxylate of the invention has a long storage life and excellent thermal stability, and accordingly is useful as a material for pharmaceutical preparation.

Form thus obtained crystalline sodium or potassium (2S,3S)-3-[[(1S)-1-isobutoxymethyl-3-methylbutyl]carbamoyl]oxirane-2-carboxylate, medicaments can be prepared.

For preparing the medicaments, the salt can be processed according to the conventional manner to give, for example, tablets, granules, powder, capsules, suspension, injection or suppository. In the pharmaceutical preparation, normal additives such as excipient, disintegrator, binder, lubricant, dye and diluent are used.

EXAMPLES

The invention is further described by the following examples. They by no means restrict the invention.

Example 1

Preparation of Free Form (B)

Crude ethyl (2S,3S)-3-[[(1S)-1-isobutoxymethyl-3-methylbutyl]carbamoyl]oxirane-2-carboxylate (164.54 g) synthesized according to the process described in Patent reference 1 was dissolved in ethanol (520 mL). While the solution was cooled with ice (at a temperature of 10° C. or below), 1 mol/L aqueous sodium hydroxide solution (522 mL) was dropped. After the solution was stirred for 1.5 hours while the temperature was kept, ethanol was removed under reduced pressure. Water (340 mL) was added, and then the mixture was filtered through Celite to remove insoluble materials. The mixture was washed twice with ethyl acetate (300 mL). While the aqueous portion was cooled with ice, 6 mol/L aqueous hydrochloric acid (110 mL) was dropped to adjust the pH value to 1 and then the mixture was extracted twice with ethyl acetate (300 mL). The ethyl acetate portion was washed with water (300 mL) and with aqueous saturated sodium chloride solution (200 mL), and then dried over anhydrous sodium sulfate. The solvent was distilled off under reduced pressure to obtain (2S,3S)-3-[[(1S)-1-isobutoxymethyl-3-methylbutyl]-carbamoyl]oxirane-2-carboxylic acid (139.61 g, 93.1%) as orange oil. The NMR data were the same as those in Example 6.

Example 2

Preparation 1 of Salt with Organic Amine (C)

(2S,3S)-3-[[(1S)-1-isobutoxymethyl-3-methylbutyl]-carbamoyl]oxirane-2-carboxylic acid (139.61 g) was dissolved in ethyl acetate (630 mL). The solution was cooled with ice (at a temperature of 10° C. or below) and cyclohexylamine (48.19 g) dissolved in ethyl acetate (190 mL) was added. The resultant mixture was stirred over-night at room temperature. The precipitated crystalline product was collected by filtration, washed with ethyl acetate, and dried in air to obtain white powdery cyclohexylamine salt of (2S,3S)-3-[[(1S)-1-isobutoxymethyl-3-methylbutyl]carbamoyl]oxirane-2-carboxylic acid (165.22 g, 88.0%). The obtained product (1.0 g) was recrystallized from ethanol/water-containing ethyl acetate, to prepare crystalline flakes (925 mg, 92.5%).

Melting point: 128° C.-129° C.;

IR (KBr) cm$^{-1}$: 3310, 2950, 2850, 1660, 1620, 1570, 1540, 1460, 1445, 1380, 1360, 1340, 1295, 1250, 1220, 1120, 945, 890; and NMR (CDCl$_3$) δ: 0.9-1.0 (12H, m), 1.2-1.8 (9H, m), 1.8-1.9 (3H, m), 2.0-2.1 (2H, m), 2.9-3.1 (1H, m), 3.2-3.3 (2H, m), 3.26 (1H, d, J=2 Hz), 3.39 (2H, d, J=4 Hz), 3.49 (1H, d, J=2 Hz), 4.1-4.2 (1H, m), 6.46 (1H, d, J=9 Hz), 7.7-8.5 (1H, broad s).

Example 3

Preparation 2 of Salt with Organic Amine (C)

(2S,3S)-3-[[(1S)-1-isobutoxymethyl-3-methylbutyl]-carbamoyl]oxirane-2-carboxylic acid (6.59 g) was dissolved in diethyl ether (67 mL), and benzathine (2.75 g) dissolved in diethyl ether (18 mL) was added while the solution was stirred at room temperature. Ethanol (6 mL) was then added to dissolve the separated oily product, and diethyl ether (84 mL) was further added. While the solution was cooled with ice, it was stirred overnight. The precipitated crystalline product was collected by filtration, washed with diethyl ether, and dried at room temperature under reduced pressure to obtain white powdery benzathine salt of (2S,3S)-3-[[(1S)-1-isobutoxymethyl-3-methylbutyl]carbamoyl]oxirane-2-carboxylic acid (7.43 g, 79.6%). The obtained product (2 g) was recrystallized from ethanol/water, to prepare the benzathine salt (1.8 g, 90.0%) in crystalline flakes.

Melting point: 63° C.;

IR (KBr) cm$^{-1}$: 3400, 3260, 2950, 2850, 1650, 1450, 1380, 1295, 1240, 1110, 890, 740; and NMR (CDCl$_3$) δ: 0.9-1.0 (12H, m), 1.3-1.5 (2H, m), 1.5-1.6 (1H, m), 1.8-1.9 (1H, m), 3.1-3.2 (4H, m), 3.9-4.0 (2H, m), 4.1-4.2 (1H, m), 6.36 (1H, d, J=9 Hz), 7.39 (5H, s).

Example 4

Preparation 3 of Salt with Organic Amine (C)

(2S,3S)-3-[[(1S)-1-isobutoxymethyl-3-methylbutyl]-carbamoyl]oxirane-2-carboxylic acid (1.31 g) was dissolved in acetone (6 mL), and meglumine (0.85 g) dissolved in water (1.5 mL) was added while the solution was stirred at room temperature. Acetone (14 mL) was further added, and then the solution was stirred overnight at room temperature. The precipitated crystalline product was collected by filtration, washed with acetone, dried in air and further dried under reduced pressure at room temperature to obtain meglumine salt of (2S,3S)-3-[[(1S)-1-isobutoxymethyl-3-methylbutyl]carbamoyl]oxirane-2-carboxylic acid (1.28 g, 61.0%) in white crystalline plates.

Melting point: 96° C.-98° C.;

IR (KBr) cm$^{-1}$: 3300, 2950, 1660, 1620, 1590, 1460, 1390, 1305, 1250, 1100, 1080, 1030, 890; and NMR (D$_2$O) δ: 0.7-0.9 (12H, m), 1.2-1.4 (2H, m), 1.5-1.6 (1H, m), 1.7-1.8 (1H, m), 2.69 (3H, s), 3.1-3.6 (15H, m), 3.7-3.8 (3H, m), 4.0-4.1 (2H, m).

Example 5

Preparation 4 of Salt with Organic Amine (C)

(2S,3S)-3-[[(1S)-1-isobutoxymethyl-3-methylbutyl]-carbamoyl]oxirane-2-carboxylic acid (660 mg) was dissolved in ethanol (3 mL), and DL-lysine (336 mg) dissolved in water (1.0 mL) was added while the solution was stirred at room temperature. The solution was condensed under reduced pressure, and ethanol (10 mL) was added. The obtained solution was stirred overnight at room temperature. The precipitated crystalline product was collected by filtration, washed with ethanol, dried in air and further dried under reduced pressure at room temperature to obtain white powdery DL-lysine salt of (2S,3S)-3-[[(1S)-1-isobutoxymethyl-3-methylbutyl]carbamoyl]oxirane-2-carboxylic acid (783 mg, 78.6%).

IR (KBr) cm$^{-1}$: 2950, 1640, 1460, 1380, 1100, 890; and

NMR (D$_2$O) δ: 0.7-0.9 (12H, m), 1.2-1.9 (10H, m), 2.93 (2H, t, J=7 Hz), 3.2-3.5 (6H, m), 3.66 (1H, t, J=6 Hz), 4.0-4.1 (1H, m).

Example 6

Preparation 1 of Free Form (D)

The cyclohexylamine salt of (2S,3S)-3-[[(1S)-1-isobutoxymethyl-3-methylbutyl]carbamoyl]oxirane-2-carboxylic acid (165.22 g) was added to a mixture of water (400 mL) and ethyl acetate (400 mL), to prepare a suspension. While the suspension was cooled with ice (at a temperature of 10° C. or below), 3 mol/L aqueous hydrochloric acid (140 mL) was dropped to adjust the pH value to approx. 3. The ethyl acetate portion was collected, and independently the aqueous portion was extracted with ethyl acetate (200 mL). The extracted liquid portion and the above-collected ethyl acetate portion were mixed, washed with water (200 mL) and with aqueous saturated sodium chloride solution (200 mL), and dried over anhydrous sodium sulfate. The solvent was distilled off under reduced pressure to obtain (2S,3S)-3-[[(1S)-1-isobutoxymethyl-3-methylbutyl]carbamoyl]oxirane-2-carboxylic acid (122.83 g, 99.9%) as yellow oil.

NMR (CDCl$_3$) δ: 0.9-1.0 (12H, m), 1.3-1.6 (3H, m), 1.8-1.9 (1H, m), 3.1-3.3 (2H, m), 3.43 (2H, d, J=4 Hz), 3.47 (1H, d, J=2 Hz), 3.71 (1H, d, J=2 Hz), 4.1-4.2 (1H, m), 6.50 (1H, d, J=9 Hz), 9.60 (1H, broad s).

Example 7

Preparation 2 of Free Form (D)

In the same manner as Example 6, (2S,3S)-3-[[(1S)-1-isobutoxymethyl-3-methylbutyl]carbamoyl]oxirane-2-carboxylic acid was prepared as yellow oil from the amine salt such as the benzathine salt, the meglumine salt or the DL-lysine salt. The NMR data were the same as those in Example 6.

Example 8

Preparation of Na Salt (E)

(2S,3S)-3-[[(1S)-1-isobutoxymethyl-3-methylbutyl]-carbamoyl]oxirane-2-carboxylic acid (48.59 g) was dissolved in acetone (245 mL), and sodium carbonate (8.51 g) dissolved in water (32.9 mL) was slowly added. The solution was stirred at room temperature to 50° C. for three hours until the deposited inorganic salt was dissolved. While the temperature was kept, acetone (200 mL) was dropped and a seed crystal was placed in the solution, and then the solution was stirred for 30 minutes. Acetone (510 mL) was again dropped, and the solution was stirred for 1 hour while the temperature was kept. While the solution was gradually cooled to room temperature, it was stirred overnight. The precipitated crystalline product was collected by filtration, washed with a mixture of 3% water-acetone (70 mL), dried in air to obtain white solid sodium (2S,3S)-3-[[(1S)-1-isobutoxymethyl-3-methylbutyl]carbamoyl]oxirane-2-carboxylate (46.1 g, 87.9%). The NMR data of the solid product were the same as those in Example 9.

Example 9

Preparations of Recrystallized Product (F) and Immediately Dried Na Crystallites (G)

The sodium (2S,3S)-3-[[(1S)-1-isobutoxymethyl-3-methylbutyl]carbamoyl]oxirane-2-carboxylate (25.18 g) prepared in Example 8 was dissolved in methanol (85 mL) at 50° C., and ethyl acetate (100 mL) was dropped while the temperature was kept. While the temperature was still kept, a seed crystal was placed in the solution, the solution was stirred for 1 hour, and ethyl acetate (150 mL) was again dropped. While the temperature was still kept, ethyl acetate (100 mL) was further dropped and furthermore ethyl acetate (75 mL) was dropped, and then the solution was stirred for 1 hour. While gradually cooled to room temperature, the solution was stirred over-night. The precipitated crystalline product was collected by filtration, washed with three portions of a mixture of ethyl acetate/methanol (5/1, 40 mL, 25 mL, 25 mL) in a stream of nitrogen gas. Before completely dried in air, the crystalline product was dried under reduced pressure at 40° C. overnight to obtain sodium (2S,3S)-3-[[(1S)-1-isobutoxymethyl-3-methylbutyl]carbamoyl]oxirane-2-carboxylate (21.1 g, 83.9%) in white crystalline needles.

Melting point: 170° C.-175° C. (dec.);

IR (KBr) cm$^{-1}$: 3255, 2950, 2860, 1670, 1630, 1550, 1460, 1435, 1395, 1365, 1310, 1260, 1110, 890; and NMR (D$_2$O) δ: 0.7-0.9 (12H, m), 1.2-1.4 (2H, m), 1.5-1.6 (1H, m), 1.7-1.8 (1H, m), 3.1-3.3 (2H, m), 3.3-3.5 (4H, m), 4.0-4.1 (1H, m).

Example 10

Preparation of K Salt (E)

The (2S,3S)-3-[[(1S)-1-isobutoxymethyl-3-methylbutyl]carbamoyl]oxirane-2-carboxylic acid (4.83 g) prepared in Example 6 or 7 was dissolved in acetone (23 mL), and potassium carbonate (1.11 g) dissolved in water (4.5 mL) was slowly added. The solution was stirred at room temperature until the deposited inorganic salt was dissolved. While the solution was heated at 50° C. in a bath, acetone (100 mL) was dropped and a seed crystal was placed in the solution, and then the solution was stirred for 30 minutes. Acetone (94 mL) was again dropped, and the solution was stirred for 1 hour while the temperature was kept. While gradually cooled to room temperature, the solution was stirred overnight. The precipitated crystalline product was collected by filtration, washed with a mixture of 2% water-acetone (20 mL), dried in air to obtain white solid potassium (2S,3S)-3-[[(1S)-1-isobutoxymethyl-3-methylbutyl]carbamoyl]oxirane-2-carboxylate (4.28 g, 81.7%). The NMR data of the solid product were the same as those in Example 11.

Example 11

Preparations of Recrystallized Product (F) and Immediately Dried K Crystallites (G)

The potassium (2S,3S)-3-[[(1S)-1-isobutoxymethyl-3-methylbutyl]carbamoyl]oxirane-2-carboxylate (500 mg) prepared in Example 10 was dissolved in methanol (3.5 mL) to prepare a solution. While the solution was heated at 50° C. in a bath, ethyl acetate (12 mL) was added and a seed crystal was placed in the solution. While the temperature was kept, the solution was stirred for 1 hour and ethyl acetate (23 mL) was again dropped. The solution was stirred for 1 hour while the temperature was still kept. While gradually cooled to room temperature, the solution was stirred overnight. The precipitated crystallites were collected by filtration, washed with a mixture of ethyl acetate/methanol (10/1, 10 mL) in a stream of nitrogen gas. Before completely dried in air, the crystalline product was dried under reduced pressure at 40° C. overnight to obtain potassium (2S,3S)-3-[[(1S)-1-isobutoxymethyl-3-methylbutyl]carbamoyl]oxirane-2-carboxylate (445 mg, 89.0%) in white crystalline needles.

Melting point: 177° C. (dec.);

IR (KBr) cm$^{-1}$: 3270, 3080, 2950, 2870, 1680, 1625, 1560, 1460, 1380, 1300, 1240, 1110, 895; and NMR (D$_2$O) δ: 0.8-0.9 (12H, m), 1.2-1.4 (2H, m), 1.5-1.6 (1H, m), 1.7-1.8 (1H, m), 3.2-3.3 (2H, m), 3.3-3.4 (4H, m), 4.0-4.1 (1H, m).

Example 12

Preparation of Na Salt (E) (Process 2)

Crude ethyl (2S,3S)-3-[([(1S)-1-isobutoxymethyl-3-methylbutyl]carbamoyl]oxirane-2-carboxylate (15.29 g) synthesized according to the process (acid chloride method) similar to that described in Patent reference 1 was dissolved in ethanol (24 mL). While the solution was stirred at room temperature, sodium carbonate (2.44 g) dissolved in water (24 mL) was dropped. After the solution was stirred at room temperature for 1 hour, it was further stirred at 90° C. to 95° C. for 2 hours. The solvent was distilled off under reduced pressure, and water (50 mL) was added to the residue. The obtained solution was washed with two portions of ethyl acetate (50 mL), and water was distilled off under reduced pressure. Acetone (400 mL) was dropped to the residue, and the obtained solution was stirred overnight at room temperature. The precipitated crystalline product was collected by filtration, washed with a mixture of 3% water-acetone (30 mL), washed again with acetone (30 mL), and dried in air to obtain white solid sodium (2S,3S)-3-[[(1S)-1-isobutoxymethyl-3-methylbutyl]carbamoyl]oxirane-2-carboxylate (10.55 g, 70.3%). The NMR data of the solid product were the same as those in Example 9.

Example 13

Preparation of Na Salt (E) (Process 2)

Crude ethyl (2S,3S)-3-[[(1S)-1-isobutoxymethyl-3-methylbutyl]carbamoyl]oxirane-2-carboxylate (7.82 g) synthesized according to the process (acid chloride method) similar to that described in Patent reference 1 was dissolved in ethanol (24 mL). While the solution was cooled with ice and stirred, 1 mol/L aqueous solution of sodium hydroxide (23.55 mL) was dropped. After the solution was stirred for 1.5 hours while the temperature was kept, the solvent was distilled off under reduced pressure. Water (39 mL) was added to the residue, and the obtained solution was washed with two portions of ethyl acetate (39 mL), and then water was distilled off under reduced pressure. Acetone (157 mL) was added to the residue, and the solution was stirred overnight at room temperature. The precipitated crystalline product was collected by filtration, washed with a mixture of 3% water-acetone (30 mL), washed again with acetone (30 mL), and dried in air to obtain white solid sodium (2S,3S)-3-[[(1S)-1-isobutoxymethyl-3-methylbutyl]carbamoyl]oxirane-2-carboxylate (5.36 g, 69.9%). The NMR data of the solid product were the same as those in Example 9.

Example 14

Purity Test on Free Form (D)

The products in the free form (D) obtained in Examples 6 and 7 were subjected to a purity test. In the test, each free form (D) gave no peak attributable to cleavage products (9.8 minutes) under the below-described HPLC conditions, while the peak was given by the free form or the metal salt thereof obtained by hydrolyzing the ester form (A) purified by a silica-gel column chromatography.

(HPLC Conditions)
 column: YMC-A302 (150×4.5 mm),
 mobile phase: a mixture of 0.1 mol/L sodium dihydrogen phosphate reagent (pH: 3.0)/acetonitrile (5:2),
 flow rate; controlled so that the retention time of (2S,3S)-3-[[(1S)-1-isobutoxymethyl-3-methylbutyl]-carbamoyl]oxirane-2-carboxylic acid would be approx. 13 minutes, and
 detector: UV (210 nm).

Example 15

Comparative Stability Test (Procedure)

As a sample, 10 mg of sodium or potassium (2S,3S)-3-[[(1S)-1-isobutoxymethyl-3-methylbutyl]carbamoyl]oxirane-2-carboxylate was weighed and placed in a test tube. After the sample was kept in a thermostat at 80° C. for three days under a light-shaded and airtight condition, the amount of remaining substance was measured by HPLC.

(HPLC Conditions)
 The same as those in Example 14.

(Conditions of DSC: Differential Scanning Calorimetry)
 Each of the sodium or potassium (2S,3S)-3-[[(1S)-1-isobutoxymethyl-3-methylbutyl]carbamoyl]oxirane-2-carboxylate (sample) and 0.01 g of α-alumina (standard) was placed in a container, and heated at temperatures elevating from room temperature to approx. 200° C. at the heating rate of 2° C./minute. (A differential scanning calorimetric thermobalance [TAS100, TG-DCS type, Rigaku Corporation] was used.)

(Results)
 The results are set forth in Table 1.

TABLE 1

|  | DSC | Remaining ratio(%) after 3 days at 80° C. | Ref. |
|---|---|---|---|
| Na salt (obtained according to the conventional process[1]) | 157° C. | 13-77 | amor. > crys[3] |
| Na salt (obtained through recrystallization and drying in air[2]) | 160-170° C. | 38-77 | amor. > crys[3] |
| Na salt (obtained in Example 9) | 170-175° C. | 95-98 | crystalline needles |
| K salt (obtained in Example 11) | 177° C. | 99.9 | crystalline needles |

[1])obtained by condensation to dryness;
[2])recrystallized and collected by filtration, and then left at room temperature; and
[3])presumed to be more in amorphous state than in crystal state.

The results in Table 1 clearly indicate that the crystalline Na salt prepared in Example 9 (in which the salt was recrystallized, collected by filtration in a stream of nitrogen gas and immediately dried) was superior in storage stability to the salt obtained by condensation to dryness (according to the conventional process) or obtained through recrystallization and drying in air. Further, the results in Table 1 indicate that the crystalline K salt prepared in Example 11 also had excellent storage stability.

What is claimed is:

1. Crystalline potassium (2S,3S)-3-[[(1S)-1-isobutoxymethyl-3-methylbutyl]carbamoyl]oxirane-2-carboxylate having the following characteristics:
    DSC: exothermic peak observed at 177° C. with weight decrease; and
    characteristic absorption bands of infrared absorption spectrum measured on KBr tablet: 3270, 3080, 2950, 2870, 1680, 1625, 1560, 1460, 1380, 1300, 1240, 1110, 895 cm$^{-1}$.

* * * * *